United States Patent [19]
Ota et al.

[11] Patent Number: 5,257,998
[45] Date of Patent: Nov. 2, 1993

[54] MEDICAL THREE-DIMENSIONAL LOCATING APPARATUS

[75] Inventors: Kosuke Ota, Hiroshima; Takaaki Takizawa, No. 23-18, Okinogami-cho, 4-chome, Fukuyama-shi, Hiroshima-ken; Giichi Nakamura; Katsushige Nakamura, both of Tokyo, all of Japan

[73] Assignees: Mitaka Kohki Co., Ltd.; Takaaki Takizawa, both of Japan

[21] Appl. No.: 913,766

[22] Filed: Jun. 30, 1992

Related U.S. Application Data

[63] Continuation of Ser. No. 571,818, Aug. 24, 1990, abandoned.

[30] Foreign Application Priority Data

Sep. 20, 1989 [JP] Japan .................. 1-242027

[51] Int. Cl.⁵ .............................................. A61B 19/00
[52] U.S. Cl. ................................ 606/130; 128/653.1; 414/917; 901/15; 901/41
[58] Field of Search .................. 128/653.1, 774, 782; 378/205, 206; 414/917; 901/15, 41; 606/130

[56] References Cited

U.S. PATENT DOCUMENTS

| | | | |
|---|---|---|---|
| 3,262,593 | 7/1966 | Hainer | 901/15 |
| 4,364,535 | 12/1982 | Itoh et al. | 901/15 |
| 4,563,567 | 1/1986 | Geffroy et al. | 901/15 |
| 4,583,538 | 4/1986 | Onik et al. | 128/653 R |
| 4,684,088 | 8/1987 | Heller | 414/917 |
| 4,760,851 | 8/1988 | Fraser et al. | 128/774 |
| 4,872,193 | 10/1989 | Elff et al. | |
| 4,974,243 | 11/1990 | McArdle et al. | 378/205 |
| 5,186,174 | 2/1993 | Schlondorff et al. | 606/130 |

FOREIGN PATENT DOCUMENTS

0293228A3  5/1988  European Pat. Off.
WO88/08282 11/1988  World Int. Prop. O.

OTHER PUBLICATIONS

Kwoh et al., "A New Computerized Tomographic-Aided Robotic Stereotaxis System", Robotics Age Jun., 1985 pp. 17-21.

*Primary Examiner*—Ruth S. Smith
*Attorney, Agent, or Firm*—Lowe, Price, LeBlanc & Becker

[57] ABSTRACT

A medical three-dimensional locating apparatus includes an arm unit comprising a first arm pivotally supported for tuning about a first axis, a second arm pivotally supported on the first arm for tuning about a second axis perpendicular to the first axis, and an indicating unit or an echo probe held on the second arm so as to be moved toward and away from the intersection point of the first and second axes. A support unit supports the arm unit, and position detectors are provided for detecting the position of the intersection point of the first and second axes and the position of the tip of the indicating unit or the like relative to the intersection point. The medical three-dimensional locating apparatus is capable of accurately reproducing the three-dimensional position data of a focus obtained through imaging diagnosis in the affected part for an actual surgical operation and readily selecting an optimum approach angle, namely, and angle of a direction to approach the focus to a reference line, through a simple operation.

6 Claims, 6 Drawing Sheets

MEDICAL THREE-DIMENSIONAL LOCATING APPARATUS

This application is a continuation of application Ser. No. 07/571,818 filed Aug. 24, 1990 now abandoned.

BACKGROUND OF THE INVENTION

1. Field of the Invention

The present invention relates to a medical three-dimensional locating apparatus and, more particularly, to a medical three-dimensional locating apparatus for encephalic surgical operation.

2. Description of the Prior Art

The diffusion of CT scanning apparatus and MRI scanning apparatus has revolutionized encephalic nerve surgery, and three-dimensional imaging diagnosis for encephalic nerve-surgical operation has replaced conventional imaging diagnosis employing simple cranial photography or cerebral angiography.

Imaging diagnosis employing a CT scanning apparatus or a MRI scanning apparatus, however, is able only to determine the position of a focus, i.e., a target, three-dimensionally and is unable to reproduce the position data obtained by imaging diagnosis in the patient's head. Although various kinds of CT-type localization encephalic surgical apparatus are being developed currently for the reproduction of an optional point in a picture obtained by CT scanning in the patient's head, the accuracy of such apparatus is not necessarily satisfactory.

Even if the accuracy of reproduction of CT locating encephalic surgical apparatus being developed is satisfactory, still another problem, specific to an encephalic surgical operation requiring craniotomy, remains unsolved. That is, in craniotomy, surgical opening of a portion of the patient's skull corresponding to the focus is not feasible even if the position of the portion corresponding to the focus is determined and the position of the portion is nearest to the focus. This case arises particularly when important nervous tissues exist between the rear-focus portion of the patient's skull and the focus. In such a case, another portion of the patient's skull which will allow craniotomy without interfering with the particularly important nervous tissues, must be opened to approach the focus even if the position of this portion is remote from the focus. Conventional CT-type localization encephalic surgical apparatus thus requires a difficult operation to approach the focus from the remote position on the patient's skull and to find the position of an optimum portion for craniotomy.

Accordingly, it is an object of the present invention to provide a medical three-dimensional locating apparatus capable of accurately reproducing three-dimensional position data representing the position of the focus in the patient's head, obtained by CT scanning or MRI scanning in actually carrying out a surgical operation, and requiring a simple operation for finding the position of an optimum portion for craniotomy.

SUMMARY OF THE INVENTION

To achieve the object, the present invention provides a medical three-dimensional locating apparatus which includes: an arm unit, comprising a first arm pivotally supported for turning about a first axis, a second arm pivotally supported for turning about a second axis perpendicular to said first axis, and an indicating unit attached to said second arm so as to be disposed coaxially with the first axis and to be movable toward and away from an intersection point of the first and second axes; a support arm supporting the arm unit so that the arm unit can optionally be moved in vertical, longitudinal and lateral directions to locate the arm unit at a selected position; and a plurality of position detectors for determining a position of said intersection point and a position of a tip of the indicating unit relative to said intersection point.

More concretely, the intersection point of the first and second axes remains fixed and the extremity of the indicating unit during use is directed toward the intersection point of the first and second axes, even though the first arm and the second arm are turned individually. Accordingly, the extremity of the indicating unit is always directed toward the focus when the intersection point of the first and second axes is located at the focus in the patient's head by moving the arm unit by the support unit. Since the extremity of the indicating unit is always directed toward the focus regardless of the position of the indicating unit, an optimum approach angle (i.e., a selected position for craniotomy) in which to approach the focus can readily be selected with reference to a picture obtained earlier by CT scanning or MRI scanning.

Since the position of the intersection point of the first and second axes and the position of the extremity of the indicating unit with respect thereto are detected by the position detectors, the three-dimensional position data obtained by a CT scanning apparatus or a MRI scanning apparatus can be accurately reproduced "in the patient's head" for a surgical operation by operating the arm unit. This operation of the arm unit is guided by a combination of data obtained by the position detectors and the position data of the focus obtained by prior CT scanning or MRI scanning of the surgical site, e.g., the patient's head, with monitoring of the operation of the arm unit performed on a computer-controlled display. The real-time localization of the focus is possible by using an echo probe instead of the indicating unit.

The above and other related objects, features and advantages of the present invention will become more apparent from the following description taken in connection with the accompanying drawings.

DETAILED DESCRIPTION OF THE PREFERRED EMBODIMENTS

Figure 1:
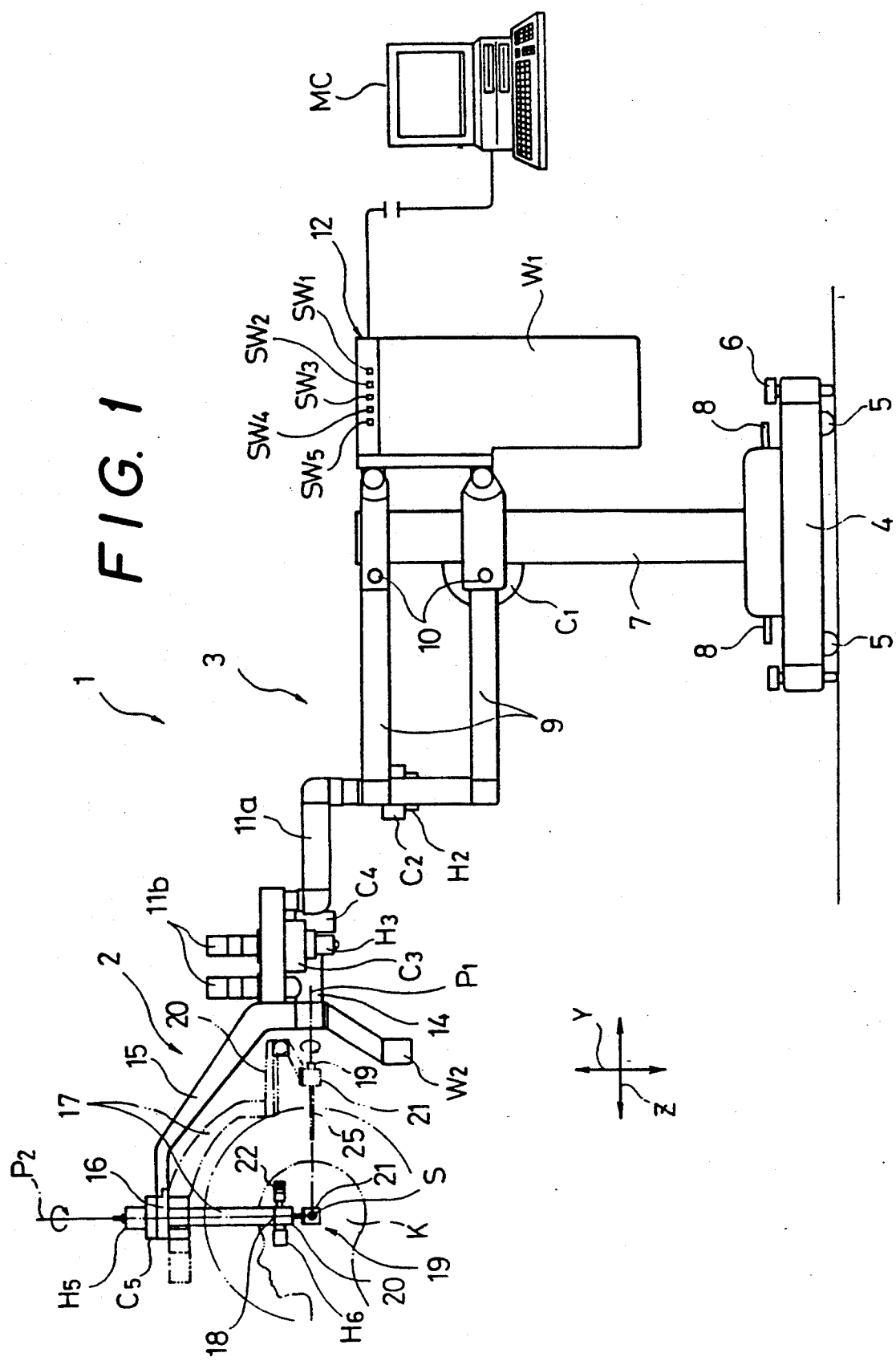
FIG. 1 is a side elevation of a medical three-dimensional locating apparatus according to a preferred embodiment of the present invention.
Figure 2:
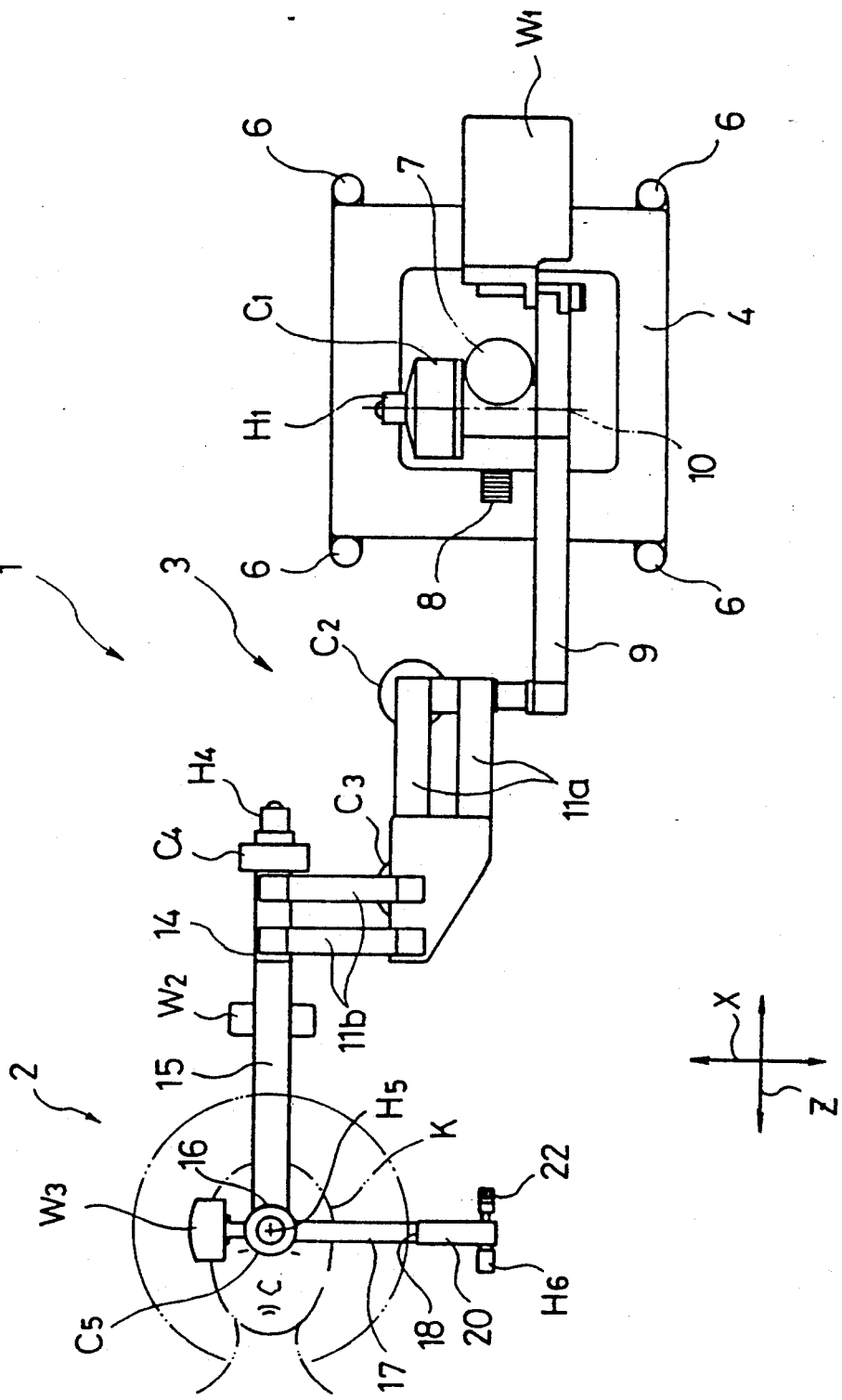
FIG. 2 is a plan view of the medical three-dimensional locating apparatus of FIG. 1.
Figure 3:
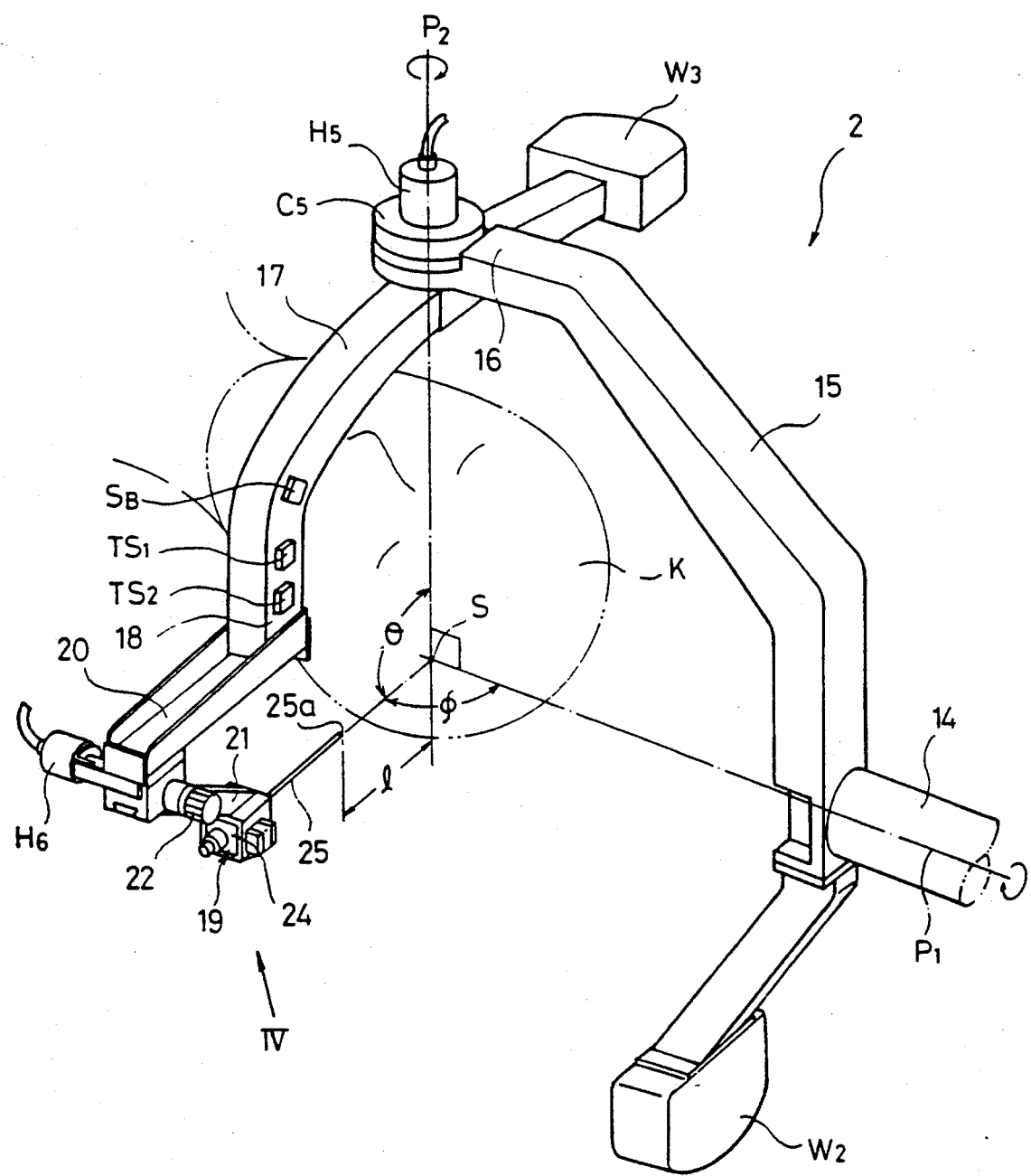
FIG. 3 is a perspective view of an arm unit.
Figure 4:
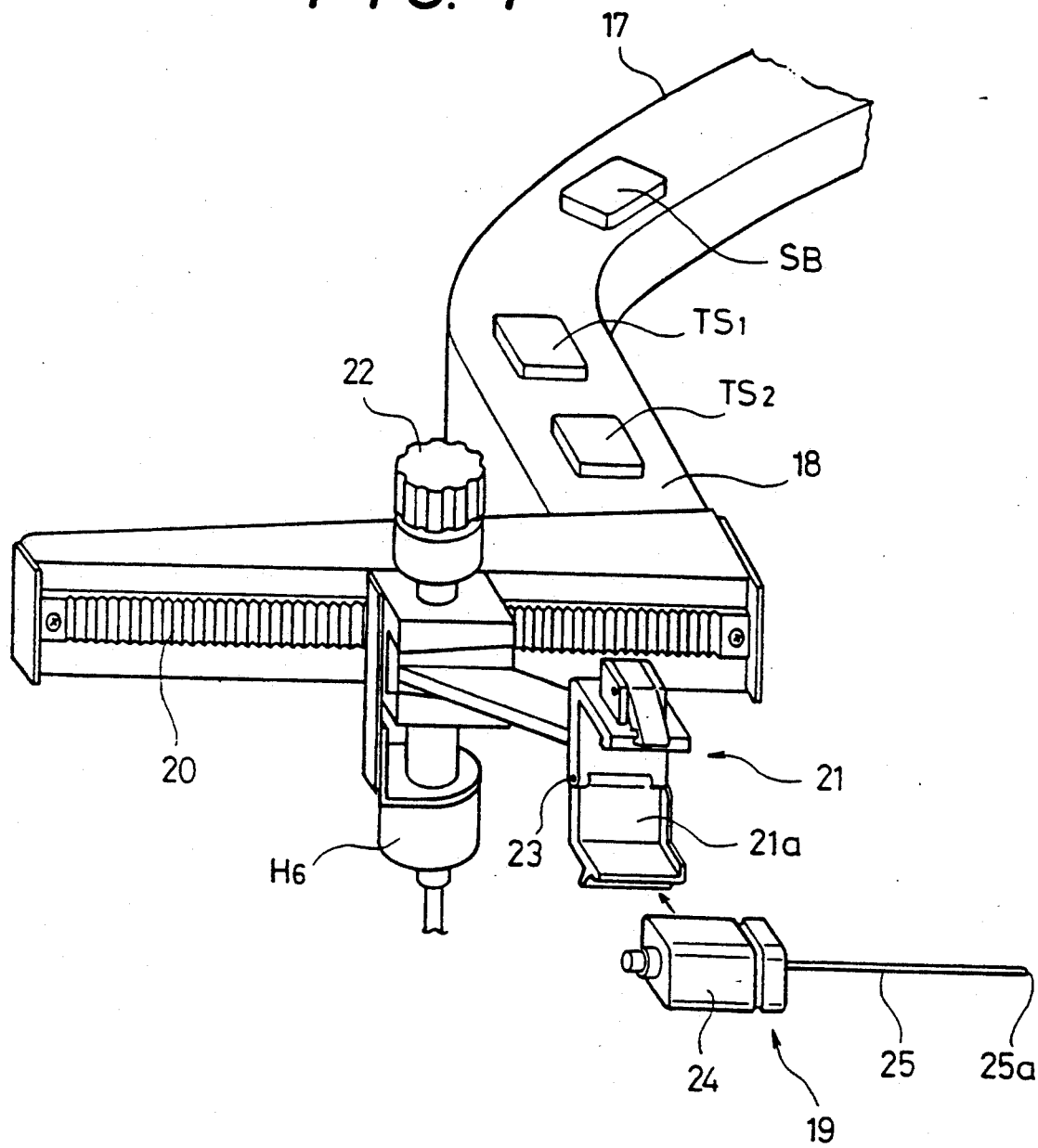
FIG. 4 is a perspective view taken in the direction of an arrow IV in FIG. 3.

Preferred embodiments of the present invention will be describe hereinafter with reference to the accompanying drawings.

Referring to FIGS. 1 to 8, a medical three-dimensional locating apparatus 1 in a preferred embodiment according to the present invention comprises an arm unit 2 to be positioned relative to the patient's head K, and a support unit 3 for supporting the arm unit 2 at an optional position. The medical three-dimensional locating apparatus 1 is controlled by a computer MC.

The support unit 3 has a base 4 provided with caster wheels 5 for free movement, and immobilizing screws 6 provided at its four corners to secure the base 4 to the floor. A post 7 is set upright in the central portion of the base 4. The post 7 can turn accurately through an angle of 180° when either of pedals 8 provided in front of and behind the post 7 is pedaled. Parallel links 9 forming a vertical-swing linkage are supported pivotally by pivots 10 on the upper portion of the post 7 for swing motion on the pivots 10 in a vertical plane to thereby shift the support unit 3 vertically. An electromagnetic clutch $C_1$ and a rotary encoder $H_1$, i.e., a position detector, are associated with the pivots 10. The electromagnetic clutch $C_1$ holds the vertical-swing linkage including the links 9 in a desired position relative to the post 7. The rotary encoder $H_1$ detects the angle of swing motion of the vertical-swing linkage including the links 9. The electromagnetic clutch $C_1$ and other electromagnetic clutches incorporated into the medical three-dimensional locating apparatus are respectively disengaged when energized and are engaged mechanically by spring mechanisms when de-energized. Accordingly, even if the medical three-dimensional locating apparatus is disconnected accidentally from the power source due to trouble, such as power failure, the vertical-swing linkage including the links 9 and the associated parts remain locked in place to secure safety.

Parallel links 11a forming a first horizontal-swing linkage for swing motion generally along the x-axis in a horizontal plane are joined pivotally to one end of the vertical-swing linkage including the links 9. A counterweight $W_1$ including an instrument unit 12 is connected to the other end of the vertical-swing linkage including the links 9 to counterbalance the weight acting on the parallel linkage of the links 9, so that the vertical-swing linkage including the links 9 can readily be operated without requiring the application of a large moving force. The first horizontal-swing linkage, including the links 11a connected to the vertical-swing linkage opposite to the counterweight $W_1$, allows the support unit 3 to perform transverse motions, namely, motions along the x-axis, in a horizontal plane. An electromagnetic clutch $C_2$ and a rotary encoder $H_2$ are connected to the joint of the vertical-swing linkage including the links 9 and the first horizontal-swing linkage including the links 11a.

A second horizontal-swing linkage formed of parallel links 11b pivotally supported on one end of the first horizontal-swing linkage including the links 11a for swing motion in a horizontal plane. The second horizontal-swing linkage including the links 11b allows the support unit 3 longitudinal motions, namely, motions along the z-axis, in a horizontal plane. An electromagnetic clutch $C_3$ and a rotary encoder $H_3$ are connected to the joint of the first horizontal-swing linkage including the links 11a and the second horizontal-swing linkage including the links 11b. The free end of the second horizontal-swing linkage including the links 11b is the extremity 14 of the support unit 3. The extremity 14 can be moved to a desired position by the combination of the vertical motions of the vertical-swing linkage including the links 9 and the horizontal and longitudinal motions of the first horizontal-swing linkage including the links 11a and the second horizontal-swing linkage including the links 11b.

The arm unit 2 is joined to the extremity 14 of the support unit 3. The arm unit 2 comprises a first arm 15 pivotally joined to the extremity 14 for turning motion about a horizontal first axis $P_1$, a vertical second arm 17 pivotally joined to the extremity 16 of the first arm 15 for turning motion about a second axis P, perpendicular to the first axis $P_1$, and an indicating unit 19 attached to the extremity 18 of the second arm 17. Indicating unit 19 is oriented to be coaxial with the first axis $P_1$ and is mounted to be capable of moving toward and away from the intersection point S of the first axis $P_1$ and the second axis $P_2$. Counterweights $W_2$ and $W_3$ are connected to the respective base ends of the first arm 15 and the second arm 17 to counterbalance the weights acting on the first arm 15 and the second arm 17, respectively, so that the first arm 15 and the second arm 17 can be readily turned by a small force and can be stopped in an optional position. The indicating unit 19 attached to the extremity 18 of the second arm 17 can be moved along a spherical surface with its center at the intersection point S by the combined turning motion of the first arm 15 and the second arm 17. A pivot supporting the first arm 15 on the extremity 14 and a pivot supporting the second arm 17 on the first arm 15 are provided with an electromagnetic clutch $C_4$ and a rotary encoder $H_4$, and an electromagnetic clutch $C_5$ and a rotary encoder $H_5$, respectively. The electromagnetic clutches $C_4$ and $C_5$ fix the first arm 15 and the second arm 17, respectively. The rotary encoders $H_4$ and $H_5$ detect the respective angles the angles $\theta$ and $\psi$ of turning the first arm 15 and the second arm 17, respectively.

A straight rack 20 is attached to the extremity of the second arm 17. A holder 21 detachably engaging the rack 20 can be moved in opposite directions along the rack 20 by turning of a knob 22. A holding member 21a of the holder 21 is swingable on a hinge 23. The cuboidal body 24 of the indicating unit 19 is positioned correctly on the holder 21 and is held firmly in place by the holding member 21a. When the cuboidal body 24 is held on the holder 21, the tip 25a of an indicating needle 25 attached to the cuboidal body 24 is directed always toward the intersection point S of the first axis $P_1$ and the second axis $P_2$. A rotary encoder $H_6$ is connected to the knob 22 for moving the holder 21 relative to the rack 20 to determine the distance 1 between the intersection point S of the first axis $P_1$ and the second axis $P_2$, and the tip 25a of the indicating needle 25 through the detection of the movement of the indicating unit 19. The holder 21 detachable from the rack 20, and the indicating unit 19 detachable from the holder 21 facilitate sterilizing of the holder 21 and the indicating unit 19.

The electromagnetic clutches $C_1$ to $C_5$ and the rotary encoders $H_1$ to $H_6$ are connected to the instrument unit 12 mounted on the counterweight $W_1$. Provided on the panel of the instrument unit 12 are switches $SW_1$ to $SW_5$ for adjusting the positions of the intersection point S of the first axis $P_1$ and the second axis $P_2$ respectively on the y-axis, the x-axis and the z-axis, the angular position $\theta$ of the indicating needle 25 with respect to the intersection point S, and the angular position $\psi$ of the indicating needle 25 with respect to the intersection point S. When the switch $SW_1$ is closed, a current is supplied to the electromagnetic clutch $C_1$ to disengage the same. The electromagnetic clutches $C_2$, $C_3$, $C_4$ and $C_5$ are controlled similarly for engagement and disengagement by operating the switches $SW_2$, $SW_3$, $SW_4$ and $SW_5$, respectively. Accordingly, when only the switch $SW_1$, for instance, is ON and the rest of the switches $SW_2$ to $SW_5$ are OFF, only the electromagnetic clutch $C_1$ is disengaged and the rest of the clutches $C_1$ to $C_5$ remain engaged, so that the intersection point S in the arm unit 2 can be moved only in vertical directions. Thus, the switches $SW_1$ to $SW_5$ are controlled selectively to enable only the desired linkage or linkages among the linkages respectively including the links 9, 11a and 11b, and/or the desired arm or arms among the arms 15 and 17 to move.

Provided on the side surface of the second arm 17 are switches $TS_1$ and $TS_2$ and a data input button SB. The switches $TS_1$ and $TS_2$ are used for controlling the electromagnetic clutches $C_4$ and $C_5$. When the switch $TS_1$ is ON, power is supplied to related ones of electromagnetic clutches $C_1$ to $C_5$ depending on which of switches $SW_1$ to $SW_5$ of the instrument unit 12 are set in their respective "OFF" positions to disengage the corresponding electromagnetic clutches among the electromagnetic clutches $C_1$ to $C_5$ of the support unit 3 in order that the support unit 3 can be freely moved. The position data of the tip 25a of the indicating needle 25 is entered by operating the data input button SB.

The computer MC is connected to the instrument unit 12. The computer MC analyzes data given thereto by the rotary encoders $H_1$ to $H_6$, and displays the results of analysis numerically on a display. The rotary encoders $H_1$ to $H_6$ are connected directly respectively to the corresponding rotary shafts of the links 9, 11a and 11b to reduce errors for accurate detection.

Figure 5:
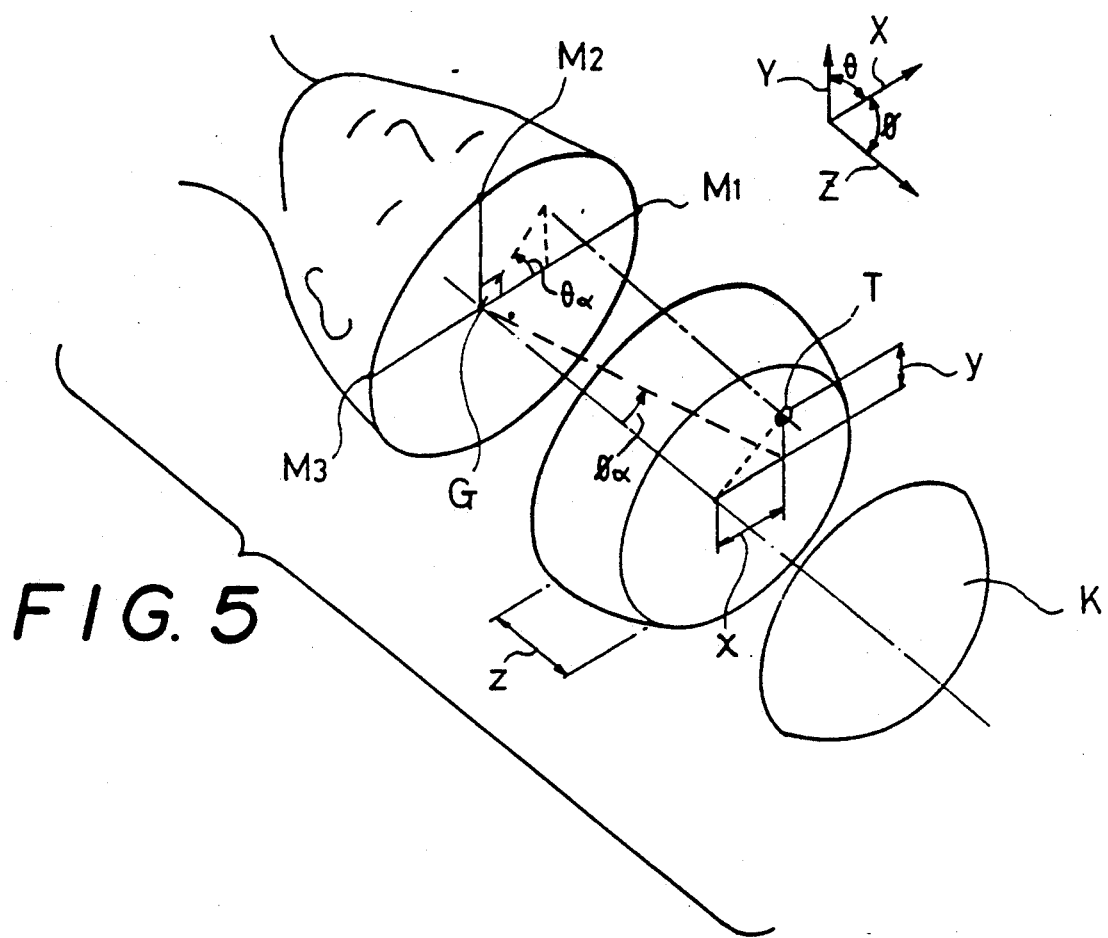
FIG. 5 is an exploded perspective view of a patient's head, showing the respective positions of an origin and the focus.

The operation of the medial three-dimensional locating apparatus will be described hereinafter. First, the patient's head K is held firmly by a fixing jig, and then three optional positions on the patient's head K are marked respectively with three marks $M_1$, $M_2$ and $M_3$. The number of positions on the patient's head K to be marked with marks need not be limited to three, but, when need be, four or more positions on the patient's head K may be marked with four or more marks. Small balls, not shown, of a material which can be detected by CT or MRI scanning, such as a metal, are secured by tapes to the patient's head K at the three positions marked respectively with the marks $M_1$, $M_2$ and $M_3$. Then, the patient's head K is set on a CT or MRI scanning apparatus for CT of MRI scanning to obtain the pictures of sections of the head K. Then, the origin G of the head K is determined with reference to the three marks $M_1$, $M_2$ and $M_3$ and, at the same time, the three-dimensional position data of the focus T with respect to the original G. The three-dimensional coordinates (x, y, z), or angles ($\theta\alpha$, $\psi\alpha$) at the origin G in the $\theta$ direction and the $\psi$ direction of the focus T can thus determined. As shown in FIG. 5, the origin G is the foot of the perpendicular from the mark $M_2$ on a straight line connecting the marks $M_1$ and $M_3$.

Figure 6:
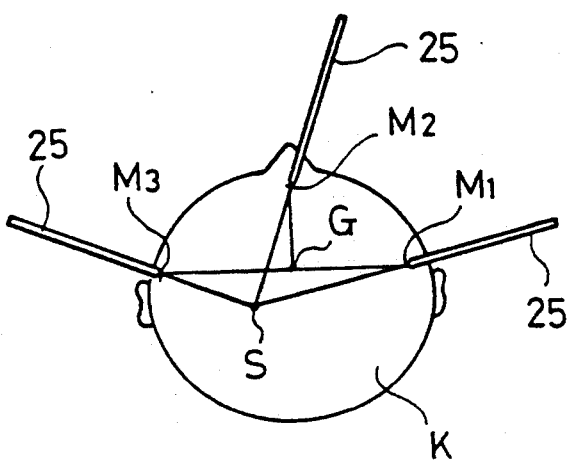
FIG. 6 is a sectional view of the patient's head, illustrating the relation between a mark and the origin.
Figure 7:
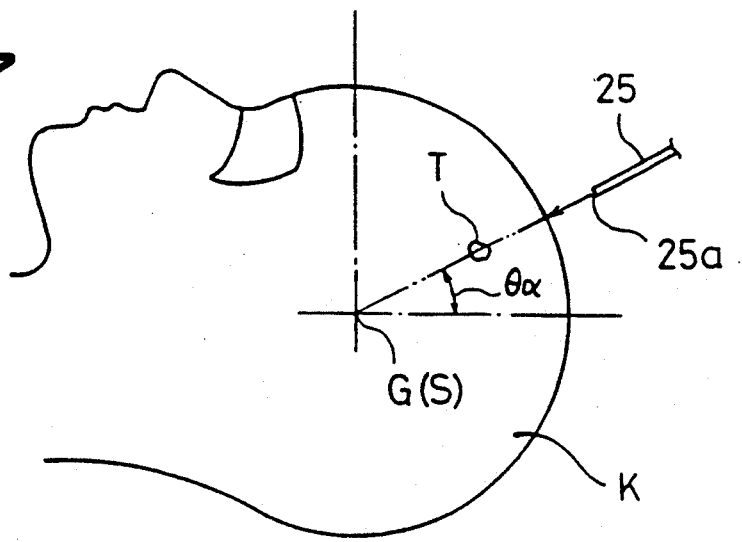
FIG. 7 is a sectional view of the patient's head, to explain an angular focus locating method for locating the focus.

After the pictures have been taken by CT or MRI scanning and the origin G has been determined, the small balls attached to the head K at the position marked with the three marks $M_1$, $M_2$ and $M_3$ are removed, and then the patient is transported with the head K held firmly by the fixing jig to an operating room. Since the head K is held immovable, the inclination of the head K with respect to a horizontal plane in the operating room is the same as that of the head K with respect to a horizontal plane (the floor) in which the head K was held during CT or MRI scanning. The patient's head K is set properly relative to the arm unit 2 of the medical three-dimensional locating apparatus 1. Then, the first arm 15 and the second arm 17 are turned to place the tip 25a of the indicating needle 25 sequentially on the marks $M_1$, $M_2$ and $M_3$ and the data input button SB is depressed to store data representing the positions of the marks $M_1$, $M_2$ and $M_3$ in the computer MC. Since the patient's head K is set arbitrarily relative to the arm unit 2, the intersection point S in which the tip 25a of the indicating needle 25 is directed and the origin G determined with reference to the marks $M_1$, $M_2$ and $M_3$ do not coincide with each other as shown in FIG. 6. The push-button of the switch $TS_1$ is depressed to disengage all the electromagnetic clutches $C_1$, $C_2$ and $C_3$ of the support unit 3, and then the arm unit 2 is moved vertically (along the y-axis), and horizontally (along the x-axis and the z-axis) to bring the intersection point S in the arm unit 2 into coincidence with the origin G in the head K.

Then, the focus T is located. An angular focus locating method of locating the focus T on the basis of the angles ($\theta\alpha$, $\psi\alpha$) at the origin G respectively in the $\theta$ direction and the $\psi$ direction will briefly be described with reference to FIG. 7. The angles of the indicating needle 25 at the origin G with respect to the $\theta$ direction and the $\psi$ direction are displayed on the monitor screen of the computer MC. The arm unit 2 is operated to bring the angles of the indicating needle 25 into coincidence respectively with the angles ($\theta\alpha$, $\psi\alpha$) at the origin G with respect to the $\theta$ direction and the $\psi$ direction determined by using the picture obtained by CT or MRI scanning. In this state, the indicating needle 25 is directed toward the focus T. The angular focus locating method, however, is unable to readily change the approach angle with respect to the focus T. A coordinate focus locating method will be described with reference to FIG. 8.

The arm unit 2 is moved on the support unit 3 on the basis of the three-dimensional coordinates (x, y, z) of the focus T determined through CT or MRI scanning to shift the intersection point S in the arm unit 2 from the origin G to the focus T within the head K. The push-button of the switch $TS_1$ is then depressed to disengage the electromagnetic clutches $C_1$, $C_2$ and $C_3$ of the support unit 3, and the arm unit 2 is moved on the support unit 3 so as to bring the present three-dimensional coordinates of the intersection point S displayed on the monitor screen of the computer MC into coincidence with the coordinates (x, y, z) of the focus T determined through CT or MRI scanning.

Upon thus obtaining the coincidence of the intersection point S with the focus T, the indicating needle 25 is directed always to the focus T (intersection point S) regardless of the approach angle, and hence the focus T can be definitely exposed through craniotomy along the direction indicated by the indicating needle 25. The depth of the focus T can be known from data provided by the encoder $H_6$ representing the positional relation between the tip 25a of the indicating needle 25 and the surface of the head K. Accordingly, an optional approach angle for reaching the focus T by surgical operation can readily be selected.

Figure 8:
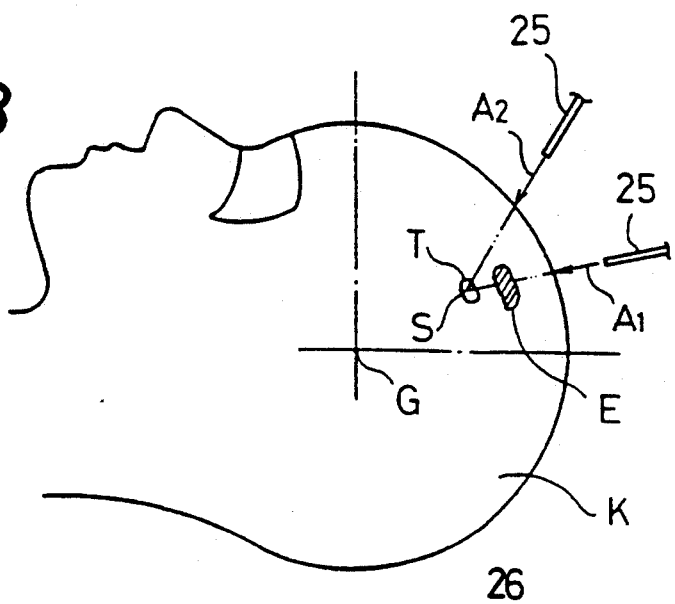
FIG. 8 is a sectional view of the patient's head, to explain a coordinate focus locating method for locating the focus.

For example, if the craniotomy is performed at an approach angle $A_1$, the focus T is at the shortest distance from the position for surgical opening on the skull. However, if important nervous tissues E or the like are situated between the position for surgical opening and the focus T as shown in FIG. 8, this position for a surgical opening cannot be used because it is possible that the important nervous tissue E or the line could be damaged if the craniotomy were to be performed at the approach angle $A_1$. In such a case, the craniotomy must be performed at an approach angle other than the approach angle $A_1$, for example, at an approach angle $A_2$. Reference to the pictures of the head obtained through CT or MRI scanning facilitates determining an optimum approach angle.

Since the medial three-dimensional locating apparatus is unnecessary after the position for surgical opening of the skull has been determined, the pedal 8 of the support unit 3 is operated to turn the support unit 3 accurately through an angle of 180° on the post 7, and then craniotomy is performed at the thus determined position for surgical opening of the skull. When it is necessary to confirm the position of the focus T again after the operation has been started, the pedal 8 is operated again to turn the support unit 3 through an angle of 180° in the opposite direction to set the arm unit 2 accurately at the initial set position with respect to the patient's head K. Thus, the arm unit 2 can readily and accurately be located again at the initial set position for the reconfirmation of the position for the appropriate surgical opening of the skull and other conditions.

In this embodiment, the intersection point S in the arm unit 2 is brought into coincidence with the origin G in the head K, and then the intersection point S is shifted from the origin G to the focus T. However, if the relation between the initial position of the intersection point S and the position of the focus T can be determined through analysis by the computer MC, the intersection point S may directly be brought into coincidence with the focus T.

The support unit 3 supporting the first arm 15 may be a known robot arm or a moving device linearly moving in the X-, Y- and the Z-direction instead of the combinations of the linkages including the links 9, 11a and 11b.

Potentiometers or suitable position detectors may be substituted for the rotary encoders $H_1$ to $H_6$.

Figure 9:
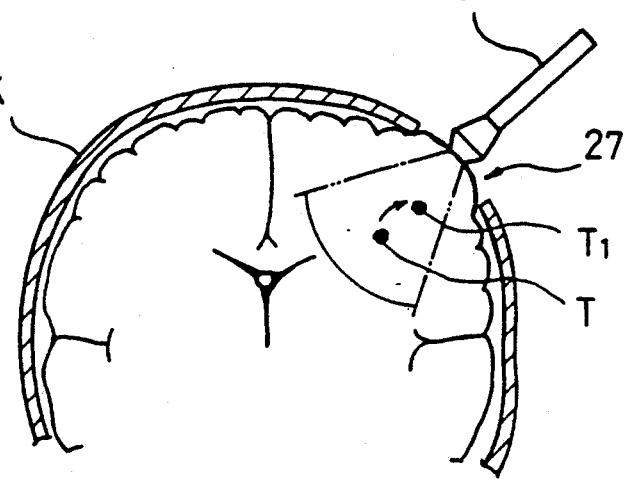
FIG. 9 is a sectional view of the patient's head, to explain a medical three-dimensional locating apparatus according to another embodiment of the present invention.

A medical three-dimensional locating apparatus in another embodiment according to the present invention will be described hereinafter with reference To FIG. 9, in which parts like or corresponding to those of the foregoing embodiment are denoted by the same reference characters and the description thereof will be omitted.

The medical three-dimensional locating apparatus in this embodiment employs an echo probe 26 instead of the indicating unit 19. The echo probe 26 is held on the holder 21 of the second arm 17. An echo picture is produced by ultrasonic waves emitted from the tip of the echo probe 26 and propagating in a sectorial region. The tip of the echo probe 26 is applied to an opening 27 formed in the head K to locate the focus T in case the focus T is caused to moved to a position $T_1$ by change in the internal pressure of the head after the opening 27 has been formed. Thus, the focus T can be located surely even if the focus T moves to the position $T_1$.

A sensor, a therapeutic apparatus for burying an electrode in the head or for perforation biopsy or an optical apparatus, such as a microscope, may be held by the holder 21 on the second arm 17.

As is apparent from the foregoing description, the intersection point of the first and second axes in the arm unit of the medical three-dimensional located apparatus in accordance with the present invention is fixed and the tip of the indicating unit is directed always toward the fixed intersecting point. Accordingly, the tip of the indicating unit is directed always toward a focus int he patient's head, once the intersection point in the arm unit is located at the focus by adjusting the position of the arm unit on the support unit, and hence an optimum approach angle (an optimum position for craniotomy) can readily be selected through a simple operation. Since the position of the intersection point of the first and second axes in the arm unit and the position of the tip of the indicating unit relative to the intersection point are detected by position detectors, the three-dimensional position data obtained through CT or MRI scanning can accurately be reproduced in the patient's head for surgical operation by bringing the data provided by the position detectors into coincidence with the three-dimensional position data of the target (focus) obtained through CT or MRI scanning, monitoring the position data provided by the position detectors and displayed on the monitor screen of the computer in digital data.

The present invention has the following effects.

Counterbalanced respectively with the counterweights, the vertical-swing linkage of the support unit and the arms can rapidly and safely be moved without requiring a large force. Since the support unit can accurately be turned through an angle of 180° when the pedal is operated, the arm unit can be moved away from the operative position to the inoperative position after determining the approach angle to avoid the arm unit interfering with the surgical operation, and the arm unit can accurately be located again at the operative position with the intersection point in the arm unit located accurately at the initial position where the intersection point was located before the arm unit was moved to the inoperative position.

The removable holder and the removable indicating unit facilitate gas-sterilization of the same.

In this disclosure, there are shown and described only the preferred embodiment of the invention, but, as aforementioned, it is to be understood that the invention is capable of use in various other combinations and environments and is capable of changes or modifications within the scope of the inventive concept as expressed herein.

What is claimed is:

1. A medical three-dimensional locating apparatus, comprising:
   an arm means unit, comprising a first arm pivotally supported for turning about a first axis, said first arm means having a first end located at said first axis and extending in a direction perpendicular to said first axis to a second end, a second arm pivotally supported to said first arm means for turning about a second axis which is oriented to be perpendicular to said first axis, said second arm means having a first end rotatably supported to the second end of the first arm means and a length extending therefrom to a distal end located on the first axis, said second arm means comprising a rack section mounted at said distal end, and an operational unit mounted to the rack section to be disposed and movable coaxially with the first axis and toward and away from an intersection point of the first and second axes;

support means for movably supporting the arm unit so that the arm unit can be controllably moved in vertical, longitudinal and lateral directions to locate the arm unit at a selected position; and a plurality of position detectors respectively mounted at selected locations on the first arm means, the second arm means, the operational unit and the support means for detecting respective positions thereof, for thereby providing signals enabling determination of both a position of said intersection point and a position of a tip of the operational unit relative to said intersection point, so that the second arm means can be moved in response to said detected positions to move said operational unit along a spherical surface about said intersection point so that said tip of the operational unit is always disposed to indicate said intersection point.

2. A medical three-dimensional locating apparatus according to claim 1, wherein:
the support means comprises a combination of a vertical-swing parallel linkage and a horizontal-swing linkage.

3. A medical three-dimensional locating apparatus according to claim 1, wherein:
the operational unit comprises an echo probe.

4. A medical three-dimensional locating apparatus according to claim 1, wherein:
the operational unit comprises an element selected from the group of elements consisting of a sensor, a therapeutic apparatus and an optical apparatus.

5. A medical three-dimensional locating apparatus according to claim 1, wherein:
the first arm means further comprises a counterweight extended from said first end of the first arm means.

6. A medical three-dimensional locating apparatus according to claim 1, wherein:
the second arm means further comprises a counterweight extended from said first end of the second arm means.

* * * * *

UNITED STATES PATENT AND TRADEMARK OFFICE
CERTIFICATE OF CORRECTION

PATENT NO. : 5,257,998

DATED : November 2, 1993

INVENTOR(S) : Kosuke OTA et al.

It is certified that error appears in the above-identified patent and that said Letters Patent is hereby corrected as shown below:

Column 8, line 11, change "int he" to --in the--;

line 61, after "arm" insert --means--.

Signed and Sealed this

Fifth Day of July, 1994

Attest:

BRUCE LEHMAN

Attesting Officer

Commissioner of Patents and Trademarks